(12) United States Patent
Curie

(10) Patent No.: US 6,887,254 B1
(45) Date of Patent: May 3, 2005

(54) DISPOSABLE LANCET DEVICE

(75) Inventor: Napoleon Curie, Frankston (AU)

(73) Assignee: N & V Curie PTY LTD, Frankston (AU)

( * ) Notice: Subject to any disclaimer, the term of this patent is extended or adjusted under 35 U.S.C. 154(b) by 215 days.

(21) Appl. No.: 10/009,946

(22) PCT Filed: Jun. 9, 2000

(86) PCT No.: PCT/AU00/00652

§ 371 (c)(1),
(2), (4) Date: Dec. 10, 2001

(87) PCT Pub. No.: WO00/76408

PCT Pub. Date: Dec. 21, 2000

(30) Foreign Application Priority Data

Jun. 10, 1999 (AU) .................................. PQ0892

(51) Int. Cl.$^7$ ............................................. A61B 17/14
(52) U.S. Cl. ..................................................... 606/181
(58) Field of Search ............................... 606/181, 182, 606/183, 185, 184

(56) References Cited

U.S. PATENT DOCUMENTS

| 4,388,925 A | 6/1983 | Burns |
|---|---|---|
| 4,449,529 A | 5/1984 | Burns et al. |
| 4,545,376 A | 10/1985 | Beiter |
| 4,553,541 A | 11/1985 | Burns |
| 4,624,253 A | 11/1986 | Burns |
| 4,653,513 A | 3/1987 | Dombrowski |
| 4,677,979 A | 7/1987 | Burns |
| 4,735,203 A | 4/1988 | Ryder et al. |
| 4,817,603 A | 4/1989 | Turner et al. |
| 4,869,249 A | 9/1989 | Crossman et al. |
| 4,889,117 A | 12/1989 | Stevens |
| 4,990,154 A | 2/1991 | Brown et al. |
| 5,100,427 A | 3/1992 | Crossman et al. |
| 5,133,370 A | 7/1992 | Duffel |
| 5,196,025 A | 3/1993 | Ranalletta et al. |
| 5,395,387 A | 3/1995 | Burns |
| 5,439,473 A | 8/1995 | Jorgensen |
| 5,478,348 A | 12/1995 | Bajada |
| 5,514,152 A | 5/1996 | Smith |
| 5,527,334 A | 6/1996 | Kanner et al. |

(Continued)

FOREIGN PATENT DOCUMENTS

CA 2025801 A 5/1991

(Continued)

Primary Examiner—Kevin T. Truong
(74) Attorney, Agent, or Firm—Knobbe, Martens, Olson & Bear, LLP

(57) ABSTRACT

A disposable lancet device adapted to pierce human skin sufficiently to let a small quantity of blood for testing. The device includes a lancet housing, a lancet body displaceably supported by the housing, and a piercing tip concealed within the housing in a rest position. The piercing tip can be integral with the lancet body or attached thereto. The device also includes an actuator for manually displacing the lancet body to expose the piercing tip under applied force and a return mechanism that returns the lancet body to the rest position when the manual displacement force is removed from the actuator. The actuator can be disabled to inhibit further manual displacement of the lancet body and exposure of the piercing tip. Thus, the piercing tip can be repeatedly exposed if desired, but can also be disabled once further use is no longer desired.

30 Claims, 1 Drawing Sheet

U.S. PATENT DOCUMENTS

| | | |
|---|---|---|
| 5,545,173 A | 8/1996 | Herbst |
| 5,554,166 A | 9/1996 | Lange et al. |
| 5,571,132 A | 11/1996 | Mawhirt et al. |
| 5,611,809 A * | 3/1997 | Marshall et al. ............ 606/181 |
| 5,624,458 A | 4/1997 | Lipscher |
| 5,630,828 A | 5/1997 | Mawhirt et al. |
| 5,643,306 A | 7/1997 | Schraga |
| 5,741,288 A | 4/1998 | Rife |
| 5,746,761 A | 5/1998 | Turchin |
| 5,908,434 A * | 6/1999 | Schraga ...................... 606/181 |
| 6,322,574 B1 * | 11/2001 | Lloyd et al. ................ 606/181 |

FOREIGN PATENT DOCUMENTS

| | | |
|---|---|---|
| EP | 0 858 289 B | 1/1996 |
| WO | WO 91/08712 | 6/1991 |
| WO | WO 92/19164 | 11/1992 |
| WO | WO 93/19671 | 10/1993 |
| WO | WO 95/10977 | 4/1995 |
| WO | WO 95/13750 | 5/1995 |
| WO | WO 95/16400 | 6/1995 |
| WO | WO 95/24868 | 9/1995 |
| WO | WO 97/43964 | 11/1997 |
| WO | WO 98/14125 | 4/1998 |
| WO | WO 98/58584 | 12/1998 |

* cited by examiner

DISPOSABLE LANCET DEVICE

RELATED APPLICATIONS

This application claims the benefit of the Australian application PQ 0892 filed Jun. 10, 1999 and the international application PCT/AU00/00652 filed Jun. 9, 2000.

This invention relates to a disposable lancet device which may be used to pierce human skin sufficiently to let a small quantity of blood for testing. In particular, it relates to a disposable lancet device of a relatively simple construction which can be used several times by a single user, but also has a disabling feature which can prevent reuse.

Lancet devices are currently available which enable a small quantity of blood to be let from an incision in human skin. Some diseases necessitate the testing of blood at regular intervals. For instance, diabetes requires testing for glucose content of blood and this may be performed on a day to day basis by many patients. As such, lancet devices which pierce the skin to let an adequate amount of blood for testing are required for use by patients in the home and also for use by nurses or medical technicians who routinely conduct such tests on patients.

In cases where several patients are tested consecutively, there is often a risk of a spread of infection by the use of a single lancet device on more than one patient. Furthermore, in instances of home use the problem of erroneous results may arise if a lancet device which has previously been used is used again some time later and has retained remnants of old blood which are subsequently included in the testing procedure. In order to counteract such problems devices which can only be used once have been proposed. Although these devices solve the problems addressed above they introduce a further problem in circumstances where a device fails to incise the skin on the first attempt, or if a device is accidentally activated, as a further attempt to incise the skin is not possible. Examples of lancet devices which can only be used once are shown in U.S. Pat. Nos. 4,735,203 and 5,554,166. The inability to repeat a failed attempt at incising the skin and the necessity of using a second device introduces additional costs to the consumer.

The problem of risk of infection may also arise if the needle or piercing tip of the lancet device is exposed and accidentally pricks a nurse or technician after the device has been used. Safety features enabling automatic retraction of the needle after piercing of the skin involve complicated mechanisms which usually include a large number of components resulting in a device which is expensive to manufacture. Examples of proposed lancet devices of a complicated nature with a large number of components are given in U.S. Pat. No. 5,554,166, mentioned above, and 5,741,288.

According to the present invention there is provided a disposable lancet device for piercing human skin comprising:

a lancet housing, a lancet body displaceably supported by the housing and having a piercing tip which is concealed within the housing in a rest position of the body, operating means engaged with the lancet body for manually displacing the lancet body to expose the piercing tip, and biasing means against which the lancet body operates as it is manually displaced to expose the piercing tip whereby the biasing means automatically retracts the lancet body to its rest position when the manual displacement force is removed from the operating means, wherein the operating means is adapted to be-disengaged from the lancet body after use to prevent subsequent manual displacement of the lancet body from its rest position.

The lancet device according to the present invention addresses the above problems in that it can be used several times by a single user, either in the home or by a person administering the incision, so that a first attempt can be repeated if it does not succeed. The device can also be disabled permanently to prevent reuse and has a concealed tip to alleviate accidental piercing of the skin. The device may also have a relatively simple construction. In particular, it avoids the use of complicated spring-loaded mechanisms in order to achieve successful incision of the skin.

The piercing tip is advantageously integral with the lancet body, and may be moulded with the lancet body in a plastics material such as polycarbonate, polystyrene or polypropylene. Polypropylene may not provide the tip with adequate piercing ability in which case polystyrene is preferred. In this embodiment, the tip is preferably formed of metal such as stainless steel. The tip may have a cylindrical body tapering to a pointed end, but preferably it is multi-sided, for example, pyramidal or flat with sharp leading edges to cut rather than just puncture the skin.

The lancet body is preferably supported for linear displacement by the housing, in which case the operating means is conveniently disposed on the axis of displacement of the lancet body, at the opposite end to the piercing tip. Thus, advantageously, the lancet body, operating means and piercing tip form a generally elongate member. However, the lancet body may be non-linearly displaceable and/or the operating means may project from the housing to one-side of the lancet body. The operating means may be connected to the lancet body by a screw thread or other connection device such as a snap-engaging means which facilitates ready separation from the lancet body to disable the lancet device after use. However, preferably the operating means is integrally moulded with the lancet body and is breakable therefrom at a line of weakness at or adjacent the juncture with the housing when the lancet body is in its rest position.

Only a short application of pressure to the manual operating means is required in use of the lancet device, such that the pressure applied to the operating means is translated to the lancet body for displacing the lancet body from its rest position, so that when the device is held against a person's skin, the piercing tip is exposed long enough to cause an incision and produce an adequate amount of blood for testing. Once manual pressure is removed from the operating means, the lancet body is automatically retracted back to the rest position with the piercing tip within the housing due to the operation of the biasing means. The biasing means may hold the lancet body in its rest position. The biasing means can take any of many forms.

In one embodiment, the biasing means comprises at least one resilient projection or leaf spring in the housing which is deformed by the lancet body or operating means as the lancet body is displaced out of its rest position. Preferably, the or each resilient projection may be attached to the housing. Further preferably, the or each resilient projection is integral with the housing and, for example, may conveniently be moulded with the housing.

Alternatively, the or each resilient projection or leaf spring, or other form of biasing means, may be integral with or attached to the lancet body, and is deformed by the housing as the lancet body is displaced out of its rest position.

In another embodiment, the biasing means may comprise a coil spring within the housing which is deformed by the lancet body or operating means as the lancet body is displaced out of its rest position.

One embodiment of a disposable lancet device in accordance with the present invention will now be described by way of example only with reference to the accompanying drawings in which.

DETAILED DESCRIPTION OF THE DRAWINGS

Figures 1, 2, 3:
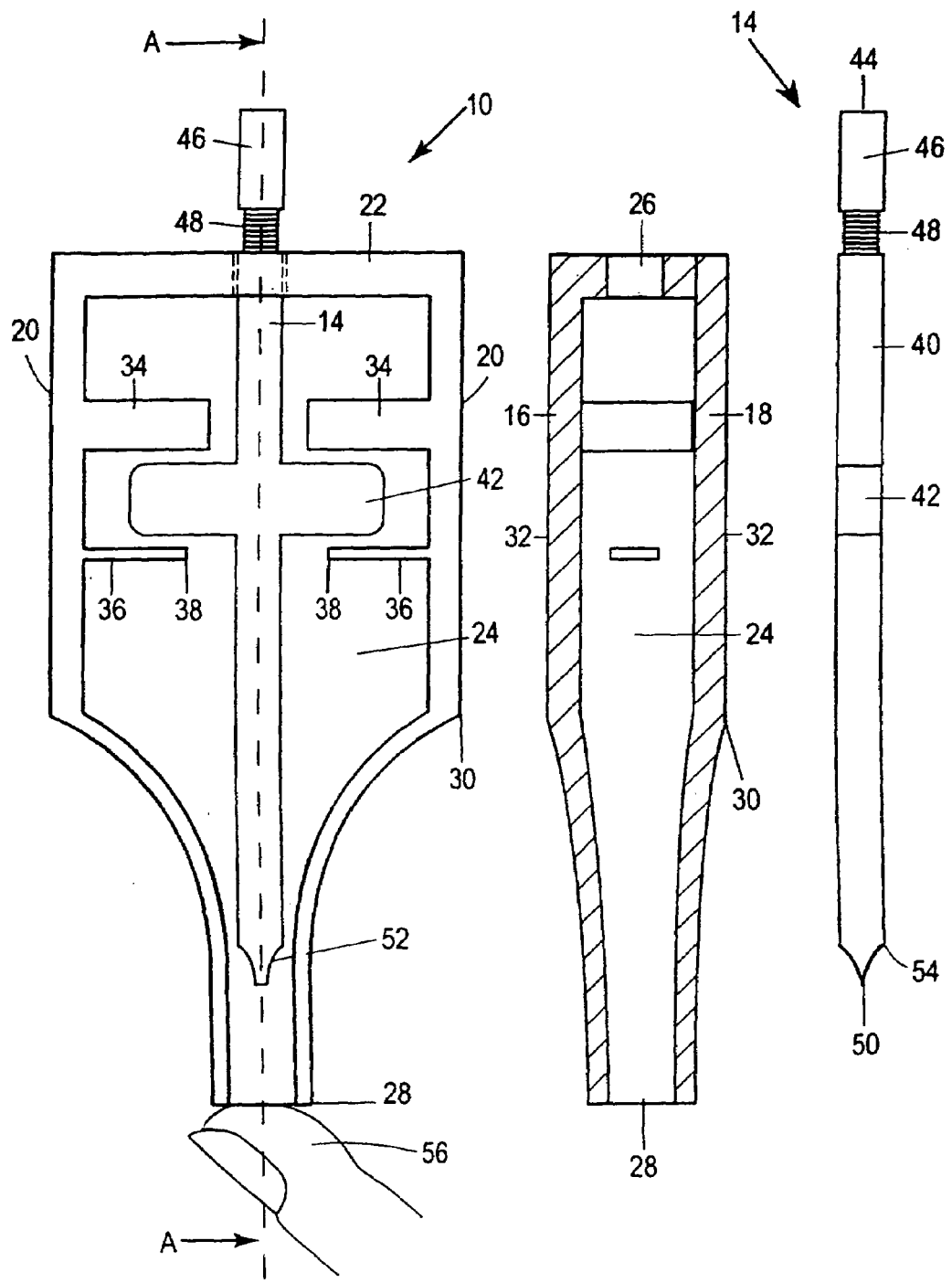
FIG. 1 is a front elevational view of the disposable lancet device, with the front removed for clarity.
FIG. 2 is a sectional view along line AA of FIG. 1, with the front cover in place and the lancet body removed.
FIG. 3 is a side view of the lancet body.

The lancet device 10 shown in the Figures comprises a housing 12 and a lancet body 14. The housing 12 is preferably moulded in polypropylene and has a front wall 18 spaced from a rear wall 16 by opposed side walls 20 and a top wall 22 extending between the side walls. The front wall 18 may be moulded separately to the remainder of the housing to facilitate the location of the lancet body 14 in the housing, or it may be integrally hinged to the remainder of the housing, for example along a join line (not shown) at the top wall 22. Either way, the front wall may be secured to the side walls 20 and top wall 22 by any suitable means including bonding with a bonding agent, heat sealing, ultrasonic or other welding or snap-engaging or other connection devices.

The housing 12 defines a passage 24 between the front and rear walls through which the lancet body 14 is manually displaceable. At one end of the passage, an opening 26 is provided in the top wall 22. At the other, the housing tapers to an opposed opening 28. Above the tapered portion 30, the housing provides opposed planar gripping surfaces 32 on the front and rear walls, both of which may be used to hold the device 10 at least until the lancet body is actuated.

Within the housing a pair of opposed stop members 34 extend from the respective side walls 20 towards each other to define a portion of the passage 24 therebetween. The stop members 34 are integrally moulded with the side walls and with the rear wall 16. Between the stop members 34 and the tapered portion 30 of the housing 12, a pair of opposed leaf springs 36 project towards each other from the side walls 20 to define another portion of the passage 24 therebetween. In contrast to the stop members 34, the leaf springs are separate from both the front and rear walls 18 and 16 so that their distal end portions 38 can resiliently flex along the passage 24. The leaf springs 36 are conveniently integral with the side walls 20 and therefore preferably injection moulded in polypropylene, but they may be separately formed, for example, in stainless steel, and for example, located in slots (not shown) in the respective side walls.

The lancet body 14 has a shaft 40 and a pair of opposed rigid wing members 42 each sized to be received between the respective stop member 34 and leaf spring 36. At its proximal end 44, the lancet body 14 has a manual operating knob 46 connected to the lancet body by a weakened portion 48 formed, for example, of reduced diameter compared to the proximal end 44 and knob 46. At its distal end 50 the lancet body 14 has a piercing tip 52 which may take any suitable form to provide a cutting point or blade. Preferably, as shown, the piercing tip is in the form of a narrow cutting edge 54.

Preferably, the lancet body 14 is also injection moulded in polypropylene, but if insufficient sharpness of the piercing tip 52 can be achieved with this material, it may instead be injection moulded in, for example, polystyrene or polycarbonate. Alternatively, instead of injection moulding the piercing tip 52 integrally with the remainder of the lancet body, it may be formed separately in the desired material and secured to the remainder of the lancet body.

The length of the shaft 40 and the relative position of the wing members 42 are such that with the wing members in the rest position between the stop members 34 and leaf springs 36 shown in FIG. 1, the operating knob 46 projects from the housing 12 with the weakened portion 48 at the juncture with the housing, but the piercing tip 52 is concealed within the tapered portion 30 of the housing. Preferably, the operating knob 46 projects sufficiently from the top wall 22 that when it is manually pressed so as to be flush with the top wall the piercing tip 52 is exposed sufficiently to just pierce the skin of the finger 56 of the patient whose blood is being let when the finger 56 is engaged with the tapered end 28 of the housing 12.

In order to assemble the device 10, the operating knob 46 is passed outwardly through the opening 26 in the top wall 22 with the front wall 18 open or removed and the shaft 40 is disposed in the passage 24 with the members 42 between the respective stop members 34 and leaf springs 36. The front wall 18 is then secured to the side walls 20 and/or top wall 22, and the device is subjected to sterilisation.

As described above, in use, the operating knob 46 is displaced manually downwardly by pressure applied directly via the thumb or forefinger of the user to expose the piercing tip 52 and pierce the skin of the patient's finger 56. The manual displacement of the knob 46 and therefore of the shaft 40 causes the wing members 42 to resiliently deform the leaf springs 36 which then automatically retract the shaft and piercing tip 52 when the manual pressure is removed from the operating knob 46. When the lancet body 14 is returned to its rest position shown in FIG. 1 by the leaf springs 36, the operating knob 46 is again exposed and may be broken off at the weakened portion 48 to prevent re-use.

Those skilled in the art will appreciate that the invention described therein is susceptible to variations and modifications other than those specifically described. It is to be understood that the invention includes all such variations and modifications which fall within its spirit and scope.

The reference to any prior art in this specification is not, and should not be taken as an acknowledgment or any form of suggestion that that prior art forms part of the common general knowledge in Australia.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

What is claimed is:

1. A disposable lancet device for piercing human skin comprising:
   a lancet housing;
   a lancet body displaceably supported by the housing and having a piercing tip which is concealed within the housing in a rest position of the body;
   an operator integral with or connected to the lancet body for manually displacing the lancet body to expose the piercing tip; and
   a return against which the lancet body operates as it is manually displaced to expose the piercing tip whereby the return automatically retracts the lancet body to its rest position when the manual displacement force is removed from the operator wherein the operator is readily manually separable from the lancet body after use to prevent subsequent manual displacement of the lancet body from its rest position.

2. The disposable lancet device of claim 1, wherein manual force applied to the operator is translated to the lancet body for displacing the lancet body from its rest position.

3. The disposable lancet device of claim 1, wherein the return holds the lancet body in its rest position.

4. The disposable lancet device of claim 1, wherein the return comprises at least one resilient projection extending from the lancet body, wherein the resilient projection is deformed by a portion of the housing when the lancet body is displaced from its rest position.

5. The disposable lancet device of claim 1, wherein the return comprises at least one resilient projection extending from the housing, wherein the resilient projection is deformed by a portion of the lancet body when the lancet body is displaced from its rest position.

6. The disposable lancet device of claim 1, wherein the return comprises a coil spring.

7. The disposable lancet device of claim 1, wherein the lancet body is supported for linear displacement by the housing.

8. The disposable lancet device of claim 1, wherein the operator is disposed on the axis of displacement of the lancet body.

9. The disposable lancet device of claim 1, wherein the lancet body, operating means and piercing tip form a generally elongate member.

10. The disposable lancet device of claim 1, wherein the lancet body is non-linearly displaceable.

11. The disposable lancet device of claim 10, wherein the operator projects from the housing to one side of the lancet body.

12. The disposable lancet device of claim 1, wherein the operator is integrally moulded with the lancet body.

13. The disposable lancet device of claim 12, wherein the operator is breakable from the lancet body at a line of weakness at or adjacent the juncture of the lancet body with the housing when the lancet body is in its rest position.

14. The disposable lancet device of claim 1, wherein the operator is connected to the lancet body by a connection device.

15. The disposable lancet device of claim 14, wherein the connection device is a snap engaging connection or screw thread.

16. The disposable lancet device of claim 1, wherein the piercing tip is secured to the lancet body.

17. The disposable lancet device of claim 1, wherein the piercing tip is integral with the lancet body.

18. The disposable lancet device of claim 16, wherein the lancet body is moulded around a mounting portion of the tip.

19. The disposable lancet device of claim 1, wherein the piercing tip and lancet body are moulded from the same or different plastics material selected from polycarbonate, polystyrene, and polypropylene.

20. The disposable lancet device of claim 18, wherein the piercing tip is formed of metal.

21. The disposable lancet device of claim 1, wherein the piercing tip has a cylindrical body tapering to a pointed end.

22. The disposable lancet device of claim 1, wherein the piercing tip is multi-sided.

23. The disposable lancet device of claim 22, wherein the tip is pyramidal or flat with sharp leading edges.

24. The disposable lancet device of claim 20, wherein the metal comprises stainless steel.

25. A multi-use, safety lancet device comprising:
a lancet housing of a first length;
a lancet body displacably positioned within the lancet housing;
a piercing tip attached to a first end of the lancet body such that the piercing tip and lancet body together are of a second length less than the first length;
a return biasing the lancet body and piercing tip to a concealed position wherein the lancet housing covers the piercing tip; and
an actuator operating the lancet body between the concealed and an operational positions wherein the piercing tip is exposed and wherein the actuator can repeatedly change between the concealed and operational positions and wherein the actuator is also disablable so as to inhibit further achievement of the operational position.

26. The device of claim 25, wherein the piercing tip and the lancet body are an integral part.

27. The device of claim 25, wherein the actuator is attached to the second end of the lancet body opposite the piercing tip such that the actuator, lancet body, and piercing tip together form a lancet assembly having a third length greater than the first length.

28. The device of claim 25, wherein the actuator is removably attached to the lancet body.

29. The device of claim 28, wherein the actuator and lancet body are an integral part and the removable attachment of the actuator to the lancet body comprises a preformed weakened region disposed between the actuator and the lancet body.

30. The device of claim 25, wherein the return comprises resilient structure formed in at least one of the lancet housing and the lancet body.

* * * * *